United States Patent [19]

Terashi et al.

[11] Patent Number: 5,151,931
[45] Date of Patent: Sep. 29, 1992

[54] THERAPEUTIC BED OF RADIOTHERAPEUTIC SYSTEM

[75] Inventors: Kozo Terashi; Toshio Oba, both of Otawara, Japan

[73] Assignee: Kabushiki Kaisha Toshiba, Kawasaki, Japan

[21] Appl. No.: 718,758

[22] Filed: Jun. 21, 1991

[30] Foreign Application Priority Data

Jun. 21, 1990 [JP] Japan .................................. 2-161208

[51] Int. Cl.$^5$ ............................................ A61N 5/10
[52] U.S. Cl. ...................................... 378/65; 378/209
[58] Field of Search ..................... 378/65, 209, 196, 20

[56] References Cited

U.S. PATENT DOCUMENTS 4,132,900 1/1979 Smith et al. ............................ 378/65

Primary Examiner—Craig E. Church
Attorney, Agent, or Firm—Oblon, Spivak, McClelland, Maier & Neustadt

[57] ABSTRACT

A therapeutic bed of a radiotherapeutic system including a radioactive ray irradiator which radiates radioactive rays for treatment of an affected portion of a patient, includes a top board on which the patient to be inspected is laid, a support base rotatably mounted on a floor of a therapeutic room, an elevating mechanism supported by the support base and supporting the top board in a vertically elevating fashion, the elevating mechanism comprising a hydraulic link mechanism of two-stage link structure, a casing covering the elevating mechanism and being constructed to be vertically contractable and expandable in association with a vertical motion of the elevating mechanism, and a hydraulic device for driving the elevating mechanism. The hydraulic driving device is disposed apart from the elevating mechanism and particularly embedded in a floor of a therapeutic room. The driving device includes a hydraulic pressure supply unit, a hydraulic pressure transfer tube and a joint rotary member connected to the elevating mechanism. The radiotherapeutic system further includes an isocenter rotation mechanism for rotating an isocenter of the irraiator, the isocenter rotation mechanism is embedded in the floor of the therapeutic room together with the driving means. The therapeutic bed is particularly applicable to the treatment of a large affected portion of the patient ranging relatively wide area.

4 Claims, 3 Drawing Sheets

THERAPEUTIC BED OF RADIOTHERAPEUTIC SYSTEM

BACKGROUND OF THE INVENTION

This invention relates to a therapeutic bed of a radiotherapeutic system intended particularly for subjecting a patient to radiotherapy in a relatively shallow and wide area of an affected portion of the patient.

A general radiotherapeutic system comprises a radioactive ray irradiator and a radiotherapeutic bed. The radioactive ray irradiator has an irradiation head for irradiating radioactive rays of a desired nature. An irradiation axis of the radioactive rays irradiated from the irradiation head intersects with a central axis of the rotation of the irradiator, and this intersecting point is an isocentric point. On the radiotherapeutic bed is mounted a top board on which a patient is placed or laid to be movable up and down, left and right, back and forth.

There has been proposed one method of treating the affected portion of the patient by utilizing the radiotherapeutic system of the type described above, in which the radioactive ray irradiator is rotated with the affected portion being adjusted exactly to the isocentric point. As other treatment methods, recently, there has also been proposed a method in which the irradiation head is positioned below a top board of a radiotherapeutic table and irradiates therefrom with the irradiation head being directed upwardly.

In the latter method, the top board is lifted upward by about several tens cm in comparison with the former method and, in this state, the irradiator is rotated about its rotation axis with the irradiation head directed upward to thereby locate the irradiator below the top board. The irradiation is then carried out from the back side of the top board so as to cover a relatively wide range of the patient body with the location of the irradiator being maintained as it is.

The reason why such upward irradiation is required is as follows. That is, radioactive rays from the irradiation head are radiated in the form of quadrangular pyramid with the radiation source as a vertex, and therefore the radioactive rays will be applied more widely as the irradiation source moves away from the patient. Consequently, when such a system is not ready for upward irradiation, the irradiation head is positioned on an upper side of the top board when treating a patient for cutaneous cancer, for example, which is distributed extensively and almost the whole body of the patient is thus irradiated relatively in a wide range. The top board should be lowered extremely. In addition, when irradiating an affected portion distributed on the back side of the patient, it is obliged for the patient to be laid on his face, thus being inconvenient and troublesome.

Now, therefore, if an upward irradiation is to be realized, the top board need not be lowered extremely and the patient then need not be laid on his face. Accordingly, the treatment for the affected portion will be effected only through a vertical movement of the top board.

To realize such upward irradiation, it will be required that a top board of the therapeutic bed is positioned apart, by about 170 cm, for example, for achieving good working condition, from a floor level in a therapeutic room in which the therapeutic bed is located, particularly in consideration of a space of a general hospital construction.

To satisfy this requirement by using a therapeutic bed of so-called pedestal type not provided with a driving mechanism including struts and others elements under the floor, it is optimal to use a hydraulic link mechanism such as an oil pressure link mechanism with a liquid as a power means also in consideration of minimizing a height of the top board from the floor level for the motion of the patient. The therapeutic bed driving mechanism is generally accommodated in a space of a casing of the therapeutic bed disposed below the top board. That is, if the driving mechanism is constructed of a mechanical element such as a gear or the like, a bulk of each element increases unavoidably and, hence, the system itself becomes large as a whole in construction.

Meanwhile, in case a single-stage link mechanism is used as the oil pressure link mechanism for establishing a moving distance of the top board in vertical movement, it is required for the link mechanism to have prolonged arm members constituting the link mechanism accordingly. Thus, when it is required for the therapeutic bed to be displaced vertically, the lengths of the respective arm members of the link mechanism are accordingly prolonged, and when the therapeutic bed is vertically lowered, the arm members of the link mechanism lie substantially horizontally in the space of the casing supporting the top board, resulting in the requirement of the horizontally elongaged large space in the casing. Furthermore, a driving mechanism for driving the link mechanism is disposed in the space of the casing near the link mechanism of the conventional therapeutic bed. This location of the link driving mechanism in the space of the casing adversely results in the horizontal elongation of the therapeutic bed itself.

In order to ovbiate this defect of the single-stage link mechanism, in the conventional technology has been also provided a two-stage link mechanism including two pair of links, each being similar to that of the single-stage link mechanism, having arm members each having a length shorter than that of the single-stage link mechanism.

According to the application of the two-stage link mechanism, the link mechanism, as a top board elevating device, has been somewhat minimized, the link mechanism driving source is still positioned horizontally protrusively in the space of the casing. Thus, the link mechanism has still been left bulky as a whole. If a strut portion in which the link mechanism is present becomes large more than necessary, not only an operating efficiency of the apparatus deteriorates, but the space available for people is reduced.

As one example of a conventional therapeutic bed, the single-stage link mechanism has a horizontal length of about 1200 cm when expanded, the two-stage link mechanism is about 900 cm, and the driving mechanism is about 400 cm in the space of the casing of the therapeutic bed.

SUMMARY OF THE INVENTION

An object of the present invention is to substantially eliminate defects and disadvantages encountered in the prior art described above and to provide a therapeutic bed of a radiotherapeutic system having a structure reduced in size and capable of improving an operating efficiency of the system.

This and other objects can be achieved according to the present invention by providing a therapeutic bed of a radiotherapeutic system including a radioactive ray irradiator which radiates radioactive rays for treatment of an affected portion of a living human body, comprising a top board on which the living human body to be inspected is laid, a support base rotatably mounted on a floor of a therapeutic room in which the therapeutic bed is disposed, an elevating mechanism supported by the support base and supporting the top board in a vertically elevating fashion, the elevating mechanism comprising a hydraulic link mechanism, a casing covering the elevating mechanism and being constructed to be vertically contractable and expandable in association with a vertical motion of the elevating mechanism, and a hydraulic means for driving the elevating mechanism, the hydraulic driving means being disposed apart from the elevating mechanism.

In a preferred embodiment, the elevating mechanism comprises two-stage link members. The hydraulic driving means comprises a hydraulic pressure supply unit, a hydraulic pressure transfer tube means of flexible structure and a rotary joint member operatively connected to the elevating mechanism, the hydraulic pressure transfer tube means being connected to the hydraulic pressure supply unit at one end and to the joint member at the other end.

The radiotherapeutic system further includes an isocenter rotation mechanism for rotating an isocenter of the irradiator, the isocenter rotation mechanism being embedded in the floor of the therapeutic room and the hydraulic driving means is embedded in the floor together with the isocenter rotation mechanism.

The therapeutic bed of the present invention is particularly applicable to the radiotherapeutic system including a radioactive ray irradiator in which a radioactive ray irradiating source is disposed to one position on a side of a back of a living human body to be inspected and which radiates radioactive rays for treatment of an affected portion in relatively wide area of a living human body.

According to the present invention, the elevating mechanism driving source is disposed apart from the elevating mechanism which is conventionally disposed in the casing of the therapeutic bed, so that the total size of the therapeutic bed is minimized in outline and hence when the strut portion of the therapeutic bed is rotated, the casing hardly comes into contact with an operator. Thus a degree of freedom of the operator becomes large, resulting in effective utilization of the space of the therapeutic room.

DESCRIPTION OF THE PREFERRED EMBODIMENTS

For a better understanding of the present invention, the conventional therapeutic bed of a radiotherapeutic system will be described hereunder with reference to FIGS. 2 and 3.

Figure 2:
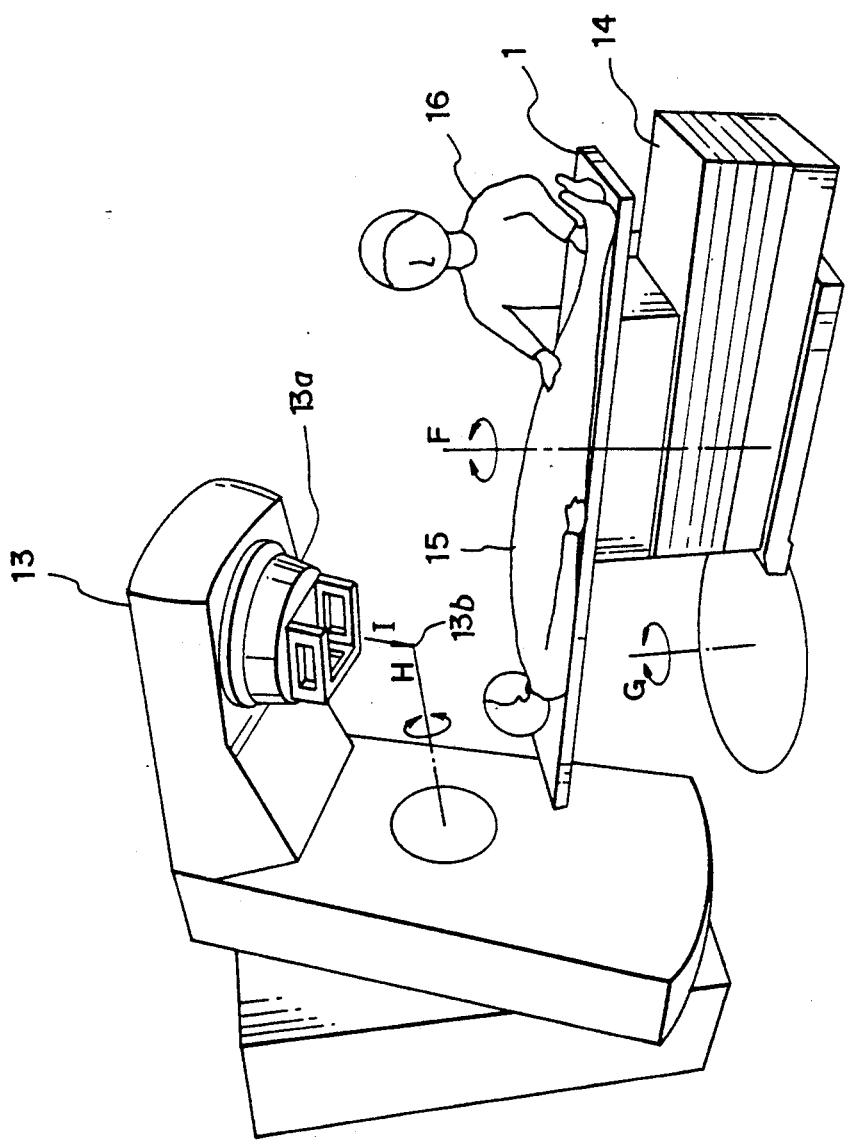
FIG. 2 is an illustration of a general radiotherapeutic system to which the present invention is applicable.

Referring to FIG. 2, a general radiotherapeutic system comprises a radioactive ray irradiator 13 and a radiotherapeutic bed 14 including a top board 1. The radioactive ray irradiator 13 has an irradiation head 13a for irradiating radioactive rays of a desired character. An irradiation axis I of the radioactive rays irradiated from the irradiation head 13a intersects with a central axis H of the rotation of the irradiator 13, and this intersecting point is called isocentric point 13b. On the radiotherapeutic bed 14 is mounted a top board on which a patient is placed or laid to be movable up and down, left and right, back and forth.

In one of methods of treating the patient for the affected portion by utilizing the radiotherapeutic system of the type described above, the radioactive ray irradiator 13 is rotated with the affected portion being adjusted exactly to the isocentric point 13b. As other methods of treating, recently, there has also been proposed a method in which the irradiation head 13a is positioned below a top board 1 of the radiotherapeutic bed and irradiates therefrom with the irradiation head 13a being directed upwardly.

Now, therefore, if an upward irradiation is to be realized, the top board need not be lowered extremely and the patient then need not be laid on his face. Accordingly, the treatment for the affected portion will be effected only through a vertical movement of the top board.

To realize such upward irradiation, it will be required that a top board of the therapeutic bed is positioned apart, for achieving good working condition, from a floor level in a therapeutic room in which the therapeutic bed is located particularly in consideration of the available space in a general hospital construction.

To satisfy this requirement by using a therapeutic bed of so-called pedestal type not provided with a driving mechanism including struts and others under the floor, it is optimal to use a hydraulic link mechanism such as an oil pressure link mechanism with a liquid as power means, also in consideration of minimizing a height of the top board from the floor level, for the motion of the patient. The therapeutic bed driving mechanism is generally accommodated in a space of a casing of the therapeutic bed disposed below the top board. That is, if the driving mechanism is constructed of a mechanical element such as a gear or the like, a bulk of each element increases unavoidably and, hence, the system itself becomes large as a whole in construction.

As the link mechanism for vertically elevating the top board, there has been proposed a single-stage link mechanism used as the oil pressure link mechanism for moving the top board in the vertical direction. This single-stage link mechanism has the defect in application to the radiotherapeutic system as described hereinbefore.

Figure 3:
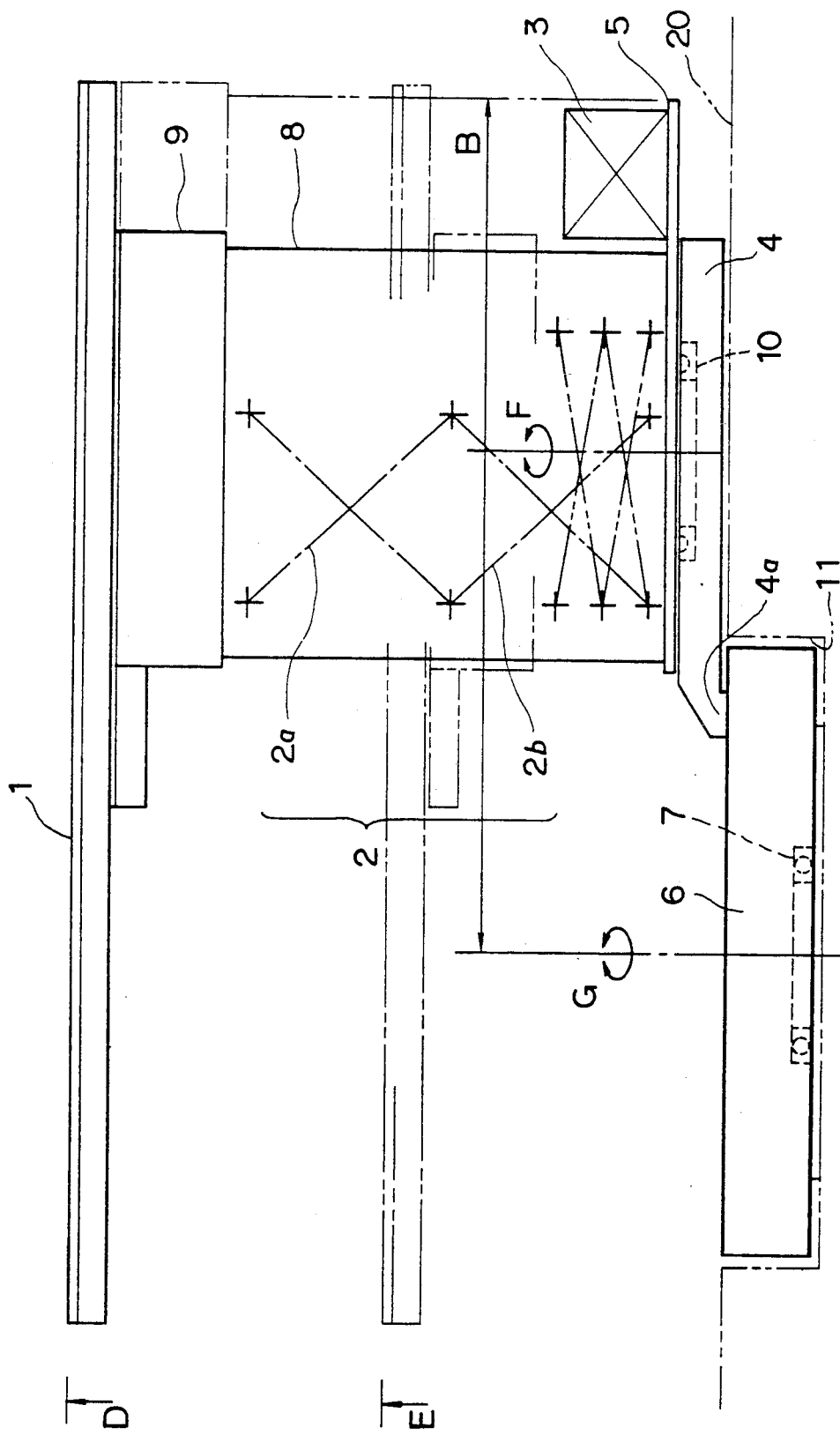
FIG. 3 is a schematic view of a conventional therapeutic bed of the radiotherapeutic system.

In order to ovbiate this defect of the single-stage link mechanism, in the conventional technology, there has been also provided a two-stage link mechanism, as shown in FIG. 3, including two pairs of links, each being similar to that of the single-stage link mechanism, having arm members each having a length shorter than that of the single-stage link mechanism.

Referring to FIG. 3, the therapeutic bed generally comprises a base support 4 settled at one end thereof to be horizontally rotatable on a floor in a therapeutic room in which the radiotherapeutic system including the therapeutic bed is disposed. A casing 8 is mounted on the base support 4 through a base plate 5 and the casing 8 has a structure contractable and expandable in a vertical direction, such as a bellows. A top board 1 is mounted on the upper portion of the casing 8 through a support table 9 into which is generally accommodated an operating means including a control panel for operating the motion of the top board 1. The top board 1 is mounted to be displacable up and down, left and right and back and forth and to be rotatable in a horizontal plane. The rotation of the top board 1 is carried out by means of a top board support strut, not shown, by rotating the same about the rotation axis F. The support strut is secured to the base plate 5 through a strut support member 10.

In the casing 8, a top board elevating mechanism, which is generally comprised by a two-stage link mechanism 2 including links 2a and 2b, is accommodated. According to the contractable or elongatable structure of the casing 8, the top board 1 is elevated so as to take vertical positions such as shown in D and E, which represent distances from the floor levels.

Furthermore, in the illustration of FIG. 3, an isocenter rotation mechanism 6 provided with its support member 7 is embedded in a recessed portion 11 formed in the floor 20 of the therapeutic room and the therapeutic bed is hence rotated through the base support 4 having one end 4a secured to the isocenter rotation mechanism 6 which is rotatable about a rotation axis G.

In one example of the conventional therapeutic bed of the structure described above, a driving source 3 for driving the top board elevating mechanism 2 is disposed near the same in the casing 8, and in the illustration, is disposed on the base plate 5.

The illustrated two-stage link type elevating mechanism includes defects or drawbacks as described hereinbefore.

The present invention conceived to substantially eliminate these defects or drawbacks will be described hereunder with reference to FIG. 1, in which like reference numerals denote like elements or members corresponding to those shown in FIGS. 2 and 3 and a further description therefor will be omitted herein.

Figure 1:
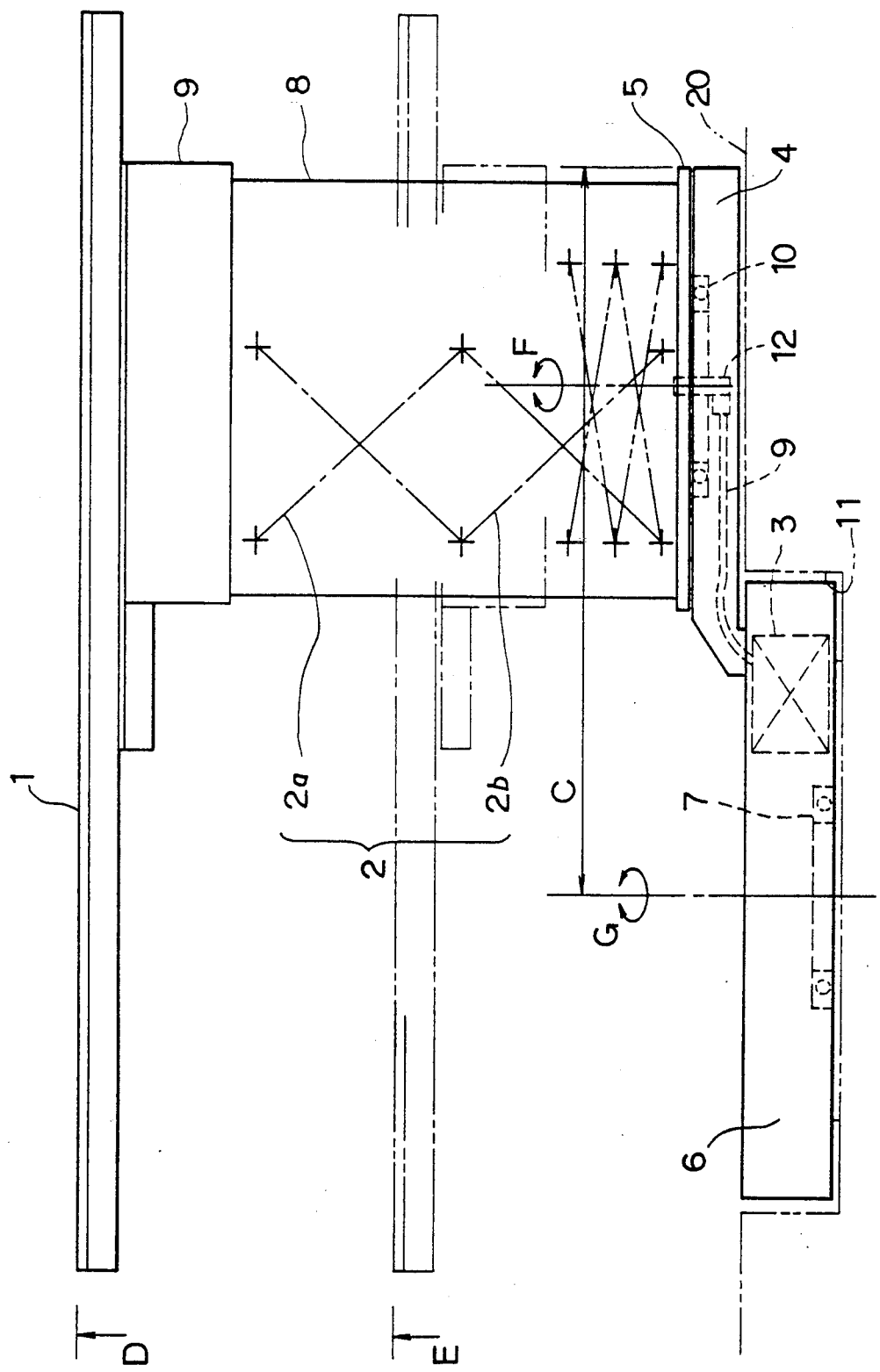
FIG. 1 is a schematic side view of a therapeutic bed of one embodiment according to the present invention.

Referring to FIG. 1, fundamental portions of the irradiator and the therapeutic bed are same as those of the prior art described hereinabove.

An oil pressure link mechanism 2 for elevating the top board 1 comprises the two-stage link members 2a and 2b and a driving source 3 for driving the link mechanism.

Particularly, the driving source 3 is embedded in the recessed portion 11, formed to the floor 20 of the therapeutic room, into which an isocenter rotating mechanism 6 which is thick and disk-like which is present at a position away from an ambient area on the floor of the casing 8, and the two-stage link motion 2, that is, below the floor level 20.

According to this embodiment, the driving source 3 as a hydraulic driving source is located in the recessed portion 11 together with or independently from the isocenter rotation mechanism 6 outside of the casing 8. The driving source 3 and the two-stage link mechanism 2 are mutually and operatively connected by a flexible high-pressure oil hose 9 having one end connected to the driving source 3 and other end connected to an hydraulic, i.e. oil, pressure rotary joint 12. The oil pressure rotary joint 12 is incorporated in the strut rotating mechanism, that is the support base 4, so as to secure a transmission of a high-pressure oil to a rotary portion.

Next described is an operation of the therapeutic bed of the aforementioned construction. First, the top board 1 is lowered and a patient is laid on his back, then the top board 1 is elevated for upward irradiation. In this case, a high-pressure oil is fed into the high-pressure oil hose 9 from the driving source 3 by a motor pump, for example. From using the flexible high-pressure oil hose, the link mechanism 2 can be separated from the driving source 3.

The whole therapeutic bed makes an isocenter rotation about the rotation axis G within an angle not to interfere with the radioactive ray irradiator 13, FIG. 2, according to the isocenter rotating mechanism 6. In this case, a support base 4 turns close to the floor. Then, the top board strut portion rotates around the rotation axis F.

The two-stage link mechanism 2 is then elevated upward by an outward high-pressure oil having passed through the high-pressure oil hose 9. While not illustrated therein, an inward low-pressure oil passes through a low-pressure oil hose to lower the two-stage link mechanism 2.

Meanwhile, an extraordinary hardness is characteristic of the high-pressure oil hose, and therefore if a flexure arises on the high-pressure oil hose 9 according to a rotation of the strut portion about the axis F, a disadvantage may result therefrom, and hence the aforementioned oil-pressure rotary joint 12 is provided therefor. In this connection, for flexure to arise on the low-pressure hose, since the hose is relatively soft, the rotary joint is not particularly required.

The top board 1 moves vertically according to an operation of the oil-pressure link motion 2 between a lowermost position E and an uppermost position D. Then, the effect of a strut miniaturization of the invention are ensured by the distances between the isocenter axis G and the outer portion of the casing 8 which are indicated in FIGS. 1 and 3 with C<B.

As described above, according to the therapeutic bed of the radiotherapeutic system of the invention, since a strut portion of the top board elevating mechanism can be miniaturized, an operating efficiency of the system is enhanced, and the surrounding free space can be enlarged. Further, the system in which the driving source 3 is provided away from the apparatus is as effective as the prior art therapeutic bed in which the top board does not ascend so high. Namely, the link mechanism driving source 3 may be embedded in another portion of the floor in the therapeutic room, disposed on the floor apart from the radiotherapeutic system at a portion such as corner portion in the room, or disposed outside the room. In any case, the driving source is connected to the link mechanism through the oil pressure hose embedded in the floor or disposed on the floor.

What is claimed is:

1. A therapeutic bed of a radiotherapeutic system including a radioactive ray irradiator in which a radioactive ray irradiating source is disposed to one position on a side of a back of a living human body to be inspected and which radiates radioactive rays for treatment of an effected portion of a living human body, comprising:

a top board on which the living human body to be inspected is to be laid, a support base rotatably mounted on a floor of a therapeutic room in which the therapeutic bed is disposed;

an elevating mechanism supported by the support base and supporting the top board for vertical elevation, said elevating mechanism comprising a hydraulic link mechanism;

a vertically expandable and contractible casing covering the elevating mechanism so as to be vertically contractible and expandable in association with a vertical motion of the elevation mechanism; and a hydraulic means for driving the elevating mechanism, said hydraulic driving means being embedded in the floor of the therapeutic room.

2. The therapeutic bed according to claim 1, wherein said elevating mechanism comprises two-stage link members.

3. The therapeutic bed according to claim 1, wherein said hydraulic driving means comprises a hydraulic pressure supply unit, a hydraulic pressure transfer tube of flexible structure and a rotary joint member operatively connected to the elevating mechanism, said hydraulic pressure transfer tube being connected to the hydraulic pressure supply unit at one end and to the rotary joint member at the other end.

4. The therapeutic bed according to claim 1, wherein the radiotherapeutic system further includes an isocenter rotation mechanism for rotating an isocenter of the irradiator, said isocenter rotation mechanism being embedded in the floor of the therapeutic room and wherein the hydraulic means is embedded in the floor together with the isocenter rotation mechanism.

* * * * *